United States Patent
Datta et al.

(10) Patent No.: US 11,732,016 B2
(45) Date of Patent: Aug. 22, 2023

(54) POLYPEPTIDE EXHIBITING GRANULOCYTE-COLONY STIMULATING FACTOR ACTIVITY

(71) Applicant: Council of Scientific & Industrial Research, New Delhi (IN)

(72) Inventors: Sonal Datta, Chandigarh (IN); Girish Sahni, Chandigarh (IN)

(73) Assignee: Council of Scientific & Industrial Research, New Delhi (IN)

(*) Notice: Subject to any disclaimer, the term of this patent is extended or adjusted under 35 U.S.C. 154(b) by 428 days.

(21) Appl. No.: 16/957,281

(22) PCT Filed: Dec. 24, 2018

(86) PCT No.: PCT/IN2018/050873
§ 371 (c)(1),
(2) Date: Jun. 23, 2020

(87) PCT Pub. No.: WO2019/130344
PCT Pub. Date: Jul. 4, 2019

(65) Prior Publication Data
US 2021/0009647 A1 Jan. 14, 2021

(30) Foreign Application Priority Data
Dec. 27, 2017 (IN) .............. 201711022403

(51) Int. Cl.
C07K 14/47 (2006.01)
A61K 47/65 (2017.01)
A61K 9/16 (2006.01)
A61K 38/19 (2006.01)
A61K 47/10 (2017.01)
C07K 1/107 (2006.01)
C07K 14/535 (2006.01)

(52) U.S. Cl.
CPC ........ *C07K 14/4705* (2013.01); *A61K 9/1605* (2013.01); *A61K 38/193* (2013.01); *A61K 47/10* (2013.01); *A61K 47/65* (2017.08); *C07K 1/1075* (2013.01); *C07K 14/535* (2013.01)

(58) Field of Classification Search
None
See application file for complete search history.

(56) References Cited

U.S. PATENT DOCUMENTS

| 5,766,897 A | 6/1998 | Braxton |
| 5,824,784 A | 10/1998 | Kinstler et al. |
| 6,608,183 B1 | 8/2003 | Cox, III |
| 6,831,158 B2 | 12/2004 | Nissen et al. |
| 7,153,943 B2 | 12/2006 | Cox, III |
| 7,214,779 B2 | 5/2007 | Cox, III |
| 7,232,885 B2 | 6/2007 | Cox, III |
| 7,253,267 B2 | 8/2007 | Cox, III |
| 7,309,781 B2 | 12/2007 | Cox, III |
| 7,314,921 B2 | 1/2008 | Cox, III |
| 7,345,149 B2 | 3/2008 | Cox, III |
| 7,560,101 B2 | 7/2009 | Cox, III |
| 7,629,314 B2 | 12/2009 | Cox, III |
| 7,732,572 B2 | 6/2010 | Cox, III |
| 7,795,396 B2 | 9/2010 | Cox, III |

(Continued)

FOREIGN PATENT DOCUMENTS

| CN | 101172161 A | 5/2008 |
| EP | 0668354 A1 | 8/1995 |

(Continued)

OTHER PUBLICATIONS

Crawford, J. et al., "Risks, Consequences, and New Directions for Its Management"; Cancer, 2004. 100(2): p. 228-37.
Lyman, G.H., "Risks and Consequences of Chemotherapy-Induced Neutropenia", Clin Cornerstone, 2006. 8 Suppl 5: p. S12-8.
Kuderer, N.M., et al., "Mortality, Morbidity, and Cost Associated with Febrile Neutropenia in Adult Cancer Patients" Cancer, 2006. 106(10): p. 2258-66.
Lyman, G.H. et al., "Prophylactic Granulocyte Colony-Stimulating Factor in Patients Receiving Dose-Intensive Cancer Chemotherapy: A Meta-analysis", Am J Med, 2002. 112(5): p. 406-11.
Metcalf, "The Colony Stimulating Factors", Cancer, 1990. 65(10): p. 2185-95.
Bradley, T.R. et al. "Stimulation by Leukaemic Sera of Colony Formation in Solid Agar Cultures by Proliferation of Mouse Bone Marrow Cells", Nature, 1967. 213(5079): p. 926-7.
Pluznik, D.H. et al. "The Induction of Clones of Normal Mast Cells by a Substance From Conditioned Medium", Experimental cell research, 1966. 43(3): p. 553-63.
Bradley, T.R. et al. The Australian journal of experimental biology and medical science, 1966. 44(3): p. 287-99.

(Continued)

*Primary Examiner* — Christina Bradley
(74) *Attorney, Agent, or Firm* — Dilworth & Barrese, LLP

(57) ABSTRACT

The present disclosure relates to a polypeptide exhibiting granulocyte-colony stimulating factor activity. The polypeptide comprises at least one non-native cysteine residue at a site selected from the group consisting of $T_1CP_2$ (SEQ ID NO: 25), $P_2CL_3$ (SEQ ID NO: 26), $L_3CG_4$ (SEQ ID NO: 27), $G_4CP_5$ (SEQ ID NO: 28), $P_5CA_6$ (SEQ ID NO: 29), $A_6CS_7$ (SEQ ID NO: 30), $S_{96}CP_{97}$ (SEQ ID NO: 31), $P_{97}CE_{98}$ (SEQ ID NO: 32), $L_{99}CG_{100}$ (SEQ ID NO: 33), $P_{101}CT_{102}$ (SEQ ID NO: 34), $E_{122}CE_{123}$ (SEQ ID NO: 35), $L_{124}CG_{125}$ (SEQ ID NO: 36), $M_{126}CA_{127}$ (SEQ ID NO: 37), $P_{138}CA_{139}$ (SEQ ID NO: 39), $A_{143}CF_{144}$ (SEQ ID NO: 40), $R_{146}CR_{147}$ (SEQ ID NO: 41), $R_{169}CH_{170}$ (SEQ ID NO: 42), $H_{170}CL_{171}$ (SEQ ID NO: 43), $L_{171}CA_{172}$ (SEQ ID NO: 44), $A_{172}CQ_{173}$ (SEQ ID NO: 45), and $Q_{173}CP_{174}$ (SEQ ID NO: 46) in an amino acid sequence having at least 90% sequence identity to sequence set forth in SEQ ID NO: 2.

10 Claims, 9 Drawing Sheets
Specification includes a Sequence Listing.

(56) References Cited

U.S. PATENT DOCUMENTS

| | | | |
|---|---|---|---|
| 7,824,669 | B2 | 11/2010 | Cox, III |
| 7,947,655 | B2 | 5/2011 | Cox, III |
| 7,964,184 | B2 | 6/2011 | Cox, III |
| 7,994,124 | B2 | 8/2011 | Cox et al. |
| 8,093,032 | B2 | 1/2012 | Kumar et al. |
| 8,133,480 | B2 | 3/2012 | Cox, III |
| 8,148,500 | B2 | 4/2012 | Cox, III |
| 8,455,434 | B2 | 6/2013 | Cox |
| 8,841,426 | B2 | 9/2014 | Kang et al. |
| 2003/0153049 | A1 | 8/2003 | Lee et al. |
| 2009/0203601 | A1 | 8/2009 | Soni et al. |
| 2013/0109623 | A1* | 5/2013 | Wang ............... A61P 37/02 530/399 |
| 2013/0165637 | A1 | 6/2013 | Xiaoqiang et al. |

FOREIGN PATENT DOCUMENTS

| | | |
|---|---|---|
| EP | 1586334 A1 | 10/2005 |
| JP | 2008-543304 A | 12/2008 |
| JP | 2009-501789 A | 1/2009 |
| JP | 2010-539898 A | 12/2010 |
| WO | 99/03887 A1 | 1/1999 |
| WO | 2006/135176 A1 | 12/2006 |
| WO | 2007/011166 A1 | 1/2007 |

OTHER PUBLICATIONS

WELTE et al., "Filgrastim (r-metHuG-CSF): The First 10 Years"; Blood, 88(6): (Sep. 1996): pp. 1907-1929.

Welte et al., "Purification and biochemical characterization of human pluripotent hematopoietic colony-stimulating factor"; Proc. Nati. Acad. Sci.; 82:, pp. 1526-1530, Mar. 1985.

Souza et al., "Recombinant Human Granulocyte Colony-Stimulating Factor: Effects on Normal and Leukemic Myeloid Cells"; Science, 232:, 1986, 61-65.

Nagata et al., "Molecular cloning and expression of cDNA for human granulocyte colony-stimulating factor"; Nature, 319:, 1986.

Keating, "Lenograstim a Review of its Use in Chemotherapy-Induced Neutropenia, for Acceleration of Neutrophil Recovery Following Haematopoietic Stem Cell Transplantation and in Peripheral Blood Stem Cell Mobilization"; Drugs 2011; 71(6): 679-707.

Van De Geijn, "Granulocyte colony-stimulating factor and its receptor in normal hematopoietic cell development and myeloid disease"; Rev Physiol Biochem Pharmacol (2003) 149: 53-71.

Fernandez-Varon et al., "Granulocyte and granulocyte macrophage colony-stimulating factors as therapy in human and veterinary medicine"; The Veterinary Journal 174 (2007) 33-41.

Tanaka et al., "Three Types of Recombinant Human Granulocyte Colonyistimulating Factor Have Equivalent Biological Activities in Monkeys"; Cytokine, 9(5): (1997) pp. 360-369.

Kuwabara et al., "Pharmacokinetics and Pharmacodynamics of a Recombinant Granulocyte Colony Human Stimulating Factor"; Drug Metabolism Reviews, 28(4): 625-658 (1996).

Kuwabara et al., "Receptor-mediated clearance of G-CSF derivative nartograstim in bone marrow of rats"; The American Physiological Society, (1995) E1-E9.

Kuwabara et al., "Renal Clearance of a Recombinant Granulocyte Colony-Stimulating Factor Nartograstim, in Rats", Pharmaceutical Research, 12(10): 1995, 1446-1469.

El Ouriaghli et al., "Neutrophil elastase enzymatically antagonizes the in vitro action of G-CSF: implications for the regulation of granulopoiesis"; Blood, 2003 101(5): 1752-1758.

Molineux, "The Design and Development of Pegfilgrastim (PEG-rmetHuG-CSF, Neulasta"; Current Pharmaceutical Design, 2004, 10: 1235-1244.

Anderson et al., "The Effect of Ammonia on the 0-Linked Glycosylation of Granulocyte Colony-Stimulating Factor Produced by Chinese Hamster Ovary Cells"; Biotechnology and Bioengineering, 47: pp. 96-105 (1995).

Halpern et al., "AlbugraninTM, a Recombinant Human Granulocyte Colony Stimulating Factor (G-CSF) Genetically Fused to Recombinant Human Albumin Induces Prolonged Myelopoietic Effects in Mice and Monkeys" Pharmaceutical Research, 19(11): 2002, 1720-1729.

Harris et al.; "Effect of Pegylation on Pharmaceuticals"; Nature Reviews Drug Discovery; 2: 2003, 214-221.

Crawford; "Pegfilgrastim Administered Once Per Cycle Reduces Incidence of Chemotherapy-Induced Neutropenia"; Drugs 2002; 62(1): 89-98.

Goodson et al.; Site-directed pegylation of recombinant interluken-2 at its glycoslation site:; Bio/Technology 8: (1990), 343-346.

Xiong et al.; "Development of tumor targeting anti-MUC-1 multimer: effects of di-scFv unpaired cysteine location on PEGylation and tumor binding"; Protein Engineering, Design & Selection, 19(8), pp. 359-367 (2006).

Ishikawa et al.; "The Substitution of Cysteine 17 of Recombinant HumanG-CSF with Alanine Greatly Enhanced its Stability"; Cell Structure and Function (17): 61-65 (1992).

Kozlowski et al., "Improvements in protein PEGylation: pegylated interferons for treatment of hepatitis C"; Journal of Controlled Release 72: (2001) 217-224.

Zhai et al., "Enhanced circulation half-life of site-specific PEGylated rhG-CSF: Optimization of PEG molecular weight" Journal of Biotechnology 142: (2009) 259-266.

Aritomi et al. "Atomic structure of the GCSF-receptor complex showing a new cytokine-receptor recognition scheme"; Nature 401: 1999, 713-717.

Tamada et al., "Homodimeric cross-over structure of the human granulocyte colony-stimulating factor (GCSF) Yeceptor signaling complex"; PNAS, 2006, 103(9), 3135-3140.

Zink et al., "Structure and Dynamics of the Human Granulocyte Colony-Stimulating Factor Protein Determined by NMR Spectroscopy. Loop Mobility in a Four-Helix-Bundle Protein"; Biochemistry, 1994, 33: 8453-8463.

Krishna Rao DV, et al., "Optimization of the AT-content of Codons Immediately Downstream of the Initiation Codon and Evaluation of Culture Conditions for High-Level Expression of Recombinant Human G-CSF in *Escherichia coli*," Mol Biotechnol (2008) 38(3):221-232.

\* cited by examiner

| | |
|---|---|
| Proximal to helix A Amino acid 1-10 | T1, P2, L3, G4, P5, A6, S7, S8 |
| Helix A Amino acid 11-39 | E33, K34 |
| AB loop Amino acid 40-70 | K40, L61 |
| Helix B Amino acid 71-91 | Q90 |
| BC loop Amino acid 92-99 | P97, E98, L99 |
| Helix C Amino acid 100-123 | P101, E122, E123 |
| CD Loop Amino acid 124-142 | P128, P138 |
| Helix D Amino acid 143-172 | R146, R147, R169, H170, L171, A172 |
| Distal to helix D Amino-acid 173-174 | Q173, P174 |

FIG. 5

| Region | Insertion at site |
|---|---|
| Proximal to helix A<br>Amino acid 1-10 | $MC T_1$, $T_1CP_2$, $P_2CL_3$, $L_3CG_4$,<br>$G_4CP_5$, $P_5CA_6$, $A_6CS_7$ |
| Helix A<br>Amino acid 11-39 | None |
| AB loop<br>Amino acid 40-70 | None |
| Helix B<br>Amino acid 71-91 | None |
| BC loop<br>Amino acid 92-99 | $S_{96}CP_{97}$, $P_{97}CE_{98}$, $L_{99}CG_{100}$ |
| Helix C<br>Amino acid 100-123 | $P_{101}CT_{102}$, $M_{121}CE_{122}$,<br>$E_{122}CE_{123}$ |
| CD Loop<br>Amino acid 124-142 | $L_{124}CG_{125}$, $M_{126}CA_{127}$,<br>$Q_{134}CG_{135}$, $P_{138}CA_{139}$ |
| Helix D<br>Amino acid 143-172 | $A_{143}CF_{144}$, $R_{146}CR_{147}$,<br>$R_{169}CH_{170}$, $H_{170}CL_{171}$,<br>$L_{171}CA_{172}$, $A_{172}CQ_{173}$ |
| Distal to helix D<br>Amino-acid 173-174 | $Q_{173}P_{174}C$, $Q_{173}CP_{174}$ |

FIG. 6

| Region | N- & C- terminal cysteine insertion and substitution sites for PEGylation |
|---|---|
| Proximal to helix A Amino acid 1-10 | $MCT_1$<br>T1, P2, L3, G4, P5, A6, S7, S8<br>N terminal linkers- $(G)Nc$, $(GGS)Nc$, $(GGGGS)Nc$, $(SGGSGG)Nc$ |
| Distal to helix D 173-174 | Q173C, P174C<br>$Q_{173}P_{174}C$<br>C terminal linkers- $(G)Nc$, $(GGS)Nc$, $(GGGGS)Nc$, $(SGGSGG)Nc$ |

| SEQUENCE ID | Modification |
|---|---|
| SEQ ID NO 1 | DNA (G-CSF) |
| SEQ ID NO 2 | Polypeptide sequence of Recombinant Human G-CSF |
| SEQ ID NO 3 | C17S |
| SEQ ID NO 4 | T1C |
| SEQ ID NO 5 | L3C |
| SEQ ID NO 6 | G4C |
| SEQ ID NO 7 | P5C |
| SEQ ID NO 8 | Q90C |
| SEQ ID NO 9 | P97C |
| SEQ ID NO 10 | E98C |
| SEQ ID NO 11 | P101C |
| SEQ ID NO 12 | Q119C |
| SEQ ID NO 13 | E122C |
| SEQ ID NO 14 | E123C |
| SEQ ID NO 15 | P128C |
| SEQ ID NO 16 | P138C |
| SEQ ID NO 17 | R146C |
| SEQ ID NO 18 | R147C |
| SEQ ID NO 19 | R169C |
| SEQ ID NO 20 | H170C |
| SEQ ID NO 21 | L171C |
| SEQ ID NO 22 | A172C |
| SEQ ID NO 23 | Q173C |
| SEQ ID NO 24 | P174C |
| SEQ ID NO 25 | T1CP2 |
| SEQ ID NO 26 | P2CL3 |
| SEQ ID NO 27 | L3CG4 |
| SEQ ID NO 28 | G4CP5 |
| SEQ ID NO 29 | P5CA6 |
| SEQ ID NO 30 | A6CS7 |
| SEQ ID NO 31 | S96CP97 |
| SEQ ID NO 32 | P97CE98 |
| SEQ ID NO 33 | L99CG100 |
| SEQ ID NO 34 | P101CT102 |
| SEQ ID NO 35 | E122CE123 |
| SEQ ID NO 36 | L124CG125 |
| SEQ ID NO 37 | M126CA127 |
| SEQ ID NO 38 | C134CG135 |
| SEQ ID NO 39 | F138CA139 |
| SEQ ID NO 40 | A143CP144 |
| SEQ ID NO 41 | R145CR147 |
| SEQ ID NO 42 | R169CH170 |
| SEQ ID NO 43 | H170CL171 |

| | |
|---|---|
| SEQ ID NO 44 | L171CA172 |
| SEQ ID NO 45 | A172CQ173 |
| SEQ ID NO 46 | Q173CP174 |
| SEQ ID NO 47 | GC |
| SEQ ID NO 48 | GGSC |
| SEQ ID NO 49 | GGGGSC |
| SEQ ID NO 50 | SGGSGGC |
| SEQ ID NO 51 | IMT1 |
| SEQ ID NO 52 | IMT2 |
| SEQ ID NO 53 | IMT3 |
| SEQ ID NO 54 | IMT4 |
| SEQ ID NO 55 | IMT5 |
| SEQ ID NO 56 | IMT6 |
| SEQ ID NO 57 | IMT7 |
| SEQ ID NO 58 | IMT8 |
| SEQ ID NO 59 | IMT9 |
| SEQ ID NO 60 | IMT10 |

FIG. 8 (CONTINUED)

SEQUENCE LISTING

<160> NUMBER OF SEQ ID NOS: 60

<210> SEQ ID NO 1
<211> LENGTH: 525
<212> TYPE: DNA
<213> ORGANISM: Homo sapiens
<220> FEATURE:
<221> NAME/KEY: gene
<222> LOCATION: (1)..(525)
<223> OTHER INFORMATION: Nucleic acid sequence for Recombinant Human
      G-CSF

<400> SEQUENCE: 1

```
atgactccat taggtccagc atctagcctg ccgcaaagtt ttctgctgaa gtgtctggaa      60
caagtccgca agattcaagg tgatggtgcg gccctgcaag aaaaactgtg cgccacctat     120
aagctgtgtc atccggaaga actggtcctg ctgggtcact cactgggcat tccgtgggcg     180
ccgctgagca gctgtccgtc gcaggccctg caactggcag ctgtctgag tcagctgcat     240 tccggcctgt ttctgtacca gggtctgctg caagcgctgg aaggcattag cccggaactg     300
ggtccgaccc tggatacgct gcaactggat gttgctgact cgcgaccac gatctggcag     360 caaatggaag aactgggcat ggcaccggct ctgcaaccga cgcaaggtgc catgccggcg     420
tttgccagtg cattccagcg tcgcgctggc ggtgtgctgg ttgcgtcaca tctgcaatca     480
tttctggaag tctcctaccg tgtcctgcgt cacctggcac agccg                    525
```

<210> SEQ ID NO 2
<211> LENGTH: 175
<212> TYPE: PRT
<213> ORGANISM: Homo sapiens
<220> FEATURE:
<221> NAME/KEY: MISC_FEATURE
<223> OTHER INFORMATION: Polypeptide sequence of rHuG-CSF

<400> SEQUENCE: 2

```
Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

<210> SEQ ID NO 3

-continued

```
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: cysteine 17 replaced to serine

<400> SEQUENCE: 3

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 4
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein threonine 1 is
      replaced by cysteine.

<400> SEQUENCE: 4

Cys Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
```

```
                   115                 120                 125

Ala Leu Gln Pro Thr Gln Gly Ala Met Pro Ala Phe Ala Ser Ala Phe
            130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

<210> SEQ ID NO 5
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein leucine 3 is
      replaced by cysteine.

<400> SEQUENCE: 5

```
Thr Pro Cys Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

<210> SEQ ID NO 6
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein glycine 4 is
      replaced by cysteine.

<400> SEQUENCE: 6

```
Thr Pro Leu Cys Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
```

```
                    35                  40                  45
Leu Leu Gly His Ser Leu Gly Ile Pro Trp Ala Pro Leu Ser Ser Cys
 50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
                100                 105                 110

Phe Ala Thr Thr Ile Trp Gln Gln Met Glu Glu Leu Gly Met Ala Pro
                115                 120                 125

Ala Leu Gln Pro Thr Gln Gly Ala Met Pro Ala Phe Ala Ser Ala Phe
            130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 7
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein proline 5 is
      replaced by cysteine.

<400> SEQUENCE: 7

Thr Pro Leu Gly Cys Ala Ser Ser Leu Pro Gln Ser Phe Leu Leu Lys
 1               5                  10                  15

Ser Leu Glu Gln Val Arg Lys Ile Gln Gly Asp Gly Ala Ala Leu Gln
                 20                  25                  30

Glu Lys Leu Cys Ala Thr Tyr Lys Leu Cys His Pro Glu Glu Leu Val
             35                  40                  45

Leu Leu Gly His Ser Leu Gly Ile Pro Trp Ala Pro Leu Ser Ser Cys
 50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
                100                 105                 110

Phe Ala Thr Thr Ile Trp Gln Gln Met Glu Glu Leu Gly Met Ala Pro
                115                 120                 125

Ala Leu Gln Pro Thr Gln Gly Ala Met Pro Ala Phe Ala Ser Ala Phe
            130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 8
<211> LENGTH: 174
<212> TYPE: PRT
<213> ORGANISM: Homo sapiens
<220> FEATURE:
```

<221> NAME/KEY: VARIANT
<222> LOCATION: (1)..(174)
<223> OTHER INFORMATION: Sequence representing single cysteine
      substitution variant made on SEQ ID NO 3, wherein glutamine 90 is
      replaced by cysteine.

<400> SEQUENCE: 8

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Cys Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 9
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein proline 97 is
      replaced by cysteine.

<400> SEQUENCE: 9

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Cys Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

```
Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 10
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein glutamic acid 98
      is replaced by cysteine.

<400> SEQUENCE: 10

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Cys Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 11
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein proline 101 is
      replaced by cysteine.

<400> SEQUENCE: 11

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45
```

Leu Leu Gly His Ser Leu Gly Ile Pro Trp Ala Pro Leu Ser Ser Cys
            50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                85                  90                  95

Pro Glu Leu Gly Cys Thr Leu Asp Thr Leu Gln Leu Asp Val Ala Asp
                100                 105                 110

Phe Ala Thr Thr Ile Trp Gln Gln Met Glu Glu Leu Gly Met Ala Pro
                115                 120                 125

Ala Leu Gln Pro Thr Gln Gly Ala Met Pro Ala Phe Ala Ser Ala Phe
            130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 12
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein glutamine 119 is
      replaced by cysteine.

<400> SEQUENCE: 12

Thr Pro Leu Gly Pro Ala Ser Ser Leu Pro Gln Ser Phe Leu Leu Lys
 1                5                  10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
 50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
                100                 105                 110

Phe Ala Thr Thr Ile Trp Cys Gln Met Glu Glu Leu Gly Met Ala Pro
                115                 120                 125

Ala Leu Gln Pro Thr Gln Gly Ala Met Pro Ala Phe Ala Ser Ala Phe
            130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 13
<211> LENGTH: 174
<212> TYPE: PRT
<213> ORGANISM: Homo sapiens
<220> FEATURE:
<221> NAME/KEY: VARIANT
<222> LOCATION: (1)..(174)

<223> OTHER INFORMATION: Sequence representing single cysteine
      substitution variant made on SEQ ID NO 3, wherein glutamic acid
      122 is replaced by cysteine.

<400> SEQUENCE: 13

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Cys Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 14
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein glutamic acid
      123 is replaced by cysteine.

<400> SEQUENCE: 14

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Cys Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 15
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein proline 128 is
      replaced by cysteine.

<400> SEQUENCE: 15

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Cys
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 16
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein proline 138 is
      replaced by cysteine.

<400> SEQUENCE: 16

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60

```
Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Cys Ala Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

<210> SEQ ID NO 17
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein arginine 146 is
      replaced by cysteine.

<400> SEQUENCE: 17

```
Thr Pro Leu Gly Pro Ala Ser Ser Leu Pro Gln Ser Phe Leu Leu Lys
 1               5                  10                  15

Ser Leu Glu Gln Val Arg Lys Ile Gln Gly Asp Gly Ala Ala Leu Gln
                 20                  25                  30

Glu Lys Leu Cys Ala Thr Tyr Lys Leu Cys His Pro Glu Glu Leu Val
             35                  40                  45

Leu Leu Gly His Ser Leu Gly Ile Pro Trp Ala Pro Leu Ser Ser Cys
         50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
        130                 135                 140

Gln Cys Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

<210> SEQ ID NO 18
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein arginine 147 is replaced by cysteine.

<400> SEQUENCE: 18

```
Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Cys Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

<210> SEQ ID NO 19
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein arginine 169 is
      replaced by cysteine.

<400> SEQUENCE: 19

```
Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
```

```
                 145                 150                 155                 160

Leu Glu Val Ser Tyr Arg Val Leu Cys His Leu Ala Gln Pro
                165                 170

<210> SEQ ID NO 20
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein histidine 170 is
      replaced by cysteine.

<400> SEQUENCE: 20

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg Cys Leu Ala Gln Pro
                165                 170

<210> SEQ ID NO 21
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein leucine 171 is
      replaced by cysteine.

<400> SEQUENCE: 21

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
```

```
                     65                  70                  75                  80
Gly Leu Phe Leu Tyr Gln Gly Leu Leu Gln Ala Leu Glu Gly Ile Ser
                 85                  90                  95
Pro Glu Leu Gly Pro Thr Leu Asp Thr Leu Gln Leu Asp Val Ala Asp
             100                 105                 110
Phe Ala Thr Thr Ile Trp Gln Gln Met Glu Glu Leu Gly Met Ala Pro
         115                 120                 125
Ala Leu Gln Pro Thr Gln Gly Ala Met Pro Ala Phe Ala Ser Ala Phe
     130                 135                 140
Gln Arg Arg Ala Gly Gly Val Leu Val Ala Ser His Leu Gln Ser Phe
145                 150                 155                 160
Leu Glu Val Ser Tyr Arg Val Leu Arg His Cys Ala Gln Pro
                165                 170
```

<210> SEQ ID NO 22
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein alanine 172 is
      replaced by cysteine.

<400> SEQUENCE: 22

```
Thr Pro Leu Gly Pro Ala Ser Ser Leu Pro Gln Ser Phe Leu Leu Lys
1               5                   10                  15
Ser Leu Glu Gln Val Arg Lys Ile Gln Gly Asp Gly Ala Ala Leu Gln
                 20                  25                  30
Glu Lys Leu Cys Ala Thr Tyr Lys Leu Cys His Pro Glu Glu Leu Val
             35                  40                  45
Leu Leu Gly His Ser Leu Gly Ile Pro Trp Ala Pro Leu Ser Ser Cys
         50                  55                  60
Pro Ser Gln Ala Leu Gln Leu Ala Gly Cys Leu Ser Gln Leu His Ser
65                  70                  75                  80
Gly Leu Phe Leu Tyr Gln Gly Leu Leu Gln Ala Leu Glu Gly Ile Ser
                 85                  90                  95
Pro Glu Leu Gly Pro Thr Leu Asp Thr Leu Gln Leu Asp Val Ala Asp
             100                 105                 110
Phe Ala Thr Thr Ile Trp Gln Gln Met Glu Glu Leu Gly Met Ala Pro
         115                 120                 125
Ala Leu Gln Pro Thr Gln Gly Ala Met Pro Ala Phe Ala Ser Ala Phe
     130                 135                 140
Gln Arg Arg Ala Gly Gly Val Leu Val Ala Ser His Leu Gln Ser Phe
145                 150                 155                 160
Leu Glu Val Ser Tyr Arg Val Leu Arg His Leu Cys Gln Pro
                165                 170
```

<210> SEQ ID NO 23
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein glutamine 173 is
      replaced by cysteine.

<400> SEQUENCE: 23

```
Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Cys Pro
                165                 170
```

<210> SEQ ID NO 24
<211> LENGTH: 174
<212> TYPE: PRT
<213> ORGANISM: Homo sapiens
<220> FEATURE:
<221> NAME/KEY: VARIANT
<222> LOCATION: (1)..(174)
<223> OTHER INFORMATION: Sequence representing single cysteine
      substitution variant made on SEQ ID NO 3, wherein proline 174 is
      replaced by cysteine.

<400> SEQUENCE: 24

```
Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160
```

```
Leu Glu Val Ser Tyr Arg Val Leu Arg His Leu Ala Gln Cys
            165                 170
```

<210> SEQ ID NO 25
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is introduced
      between threonine 1 and proline 2

<400> SEQUENCE: 25

```
Thr Cys Pro Leu Gly Pro Ala Ser Ser Leu Pro Gln Ser Phe Leu Leu
1               5                   10                  15

Lys Ser Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

<210> SEQ ID NO 26
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is introduced
      between proline 2 and leucine 3.

<400> SEQUENCE: 26

```
Thr Pro Cys Leu Gly Pro Ala Ser Ser Leu Pro Gln Ser Phe Leu Leu
1               5                   10                  15

Lys Ser Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
50                  55                  60

Cys Pro Ser Gln Ala Leu Gln Leu Ala Gly Cys Leu Ser Gln Leu His
65                  70                  75                  80
```

```
Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

<210> SEQ ID NO 27
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is inserted between
      leucine 3 and glycine 4

<400> SEQUENCE: 27

```
Thr Pro Leu Cys Gly Pro Ala Ser Ser Leu Pro Gln Ser Phe Leu Leu
1               5                   10                  15

Lys Ser Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

<210> SEQ ID NO 28
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is inserted between
      glycine 4 and proline 5

<400> SEQUENCE: 28

```
Thr Pro Leu Gly Cys Pro Ala Ser Ser Leu Pro Gln Ser Phe Leu Leu
1               5                   10                  15

Lys Ser Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
                130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

<210> SEQ ID NO 29
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is introduced
      between proline 5 and alanine 6.

<400> SEQUENCE: 29

```
Thr Pro Leu Gly Pro Cys Ala Ser Ser Leu Pro Gln Ser Phe Leu Leu
1               5                   10                  15

Lys Ser Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
                130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

<210> SEQ ID NO 30
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is introduced
      between alanine 6 and serine 7.

<400> SEQUENCE: 30

Thr Pro Leu Gly Pro Ala Cys Ser Ser Leu Pro Gln Ser Phe Leu Leu
1               5                   10                  15

Lys Ser Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 31
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is introduced
      between serine 96 and proline 97.

<400> SEQUENCE: 31

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

```
Cys Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 32
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is introduced
      between proline 97 and glutamic acid 98.

<400> SEQUENCE: 32

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Cys Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 33
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is introduced
      between leucine 99 and glycine 100.

<400> SEQUENCE: 33

Thr Pro Leu Gly Pro Ala Ser Ser Leu Pro Gln Ser Phe Leu Leu Lys
1               5                   10                  15
```

```
Ser Leu Glu Gln Val Arg Lys Ile Gln Gly Asp Gly Ala Ala Leu Gln
         20                  25                  30

Glu Lys Leu Cys Ala Thr Tyr Lys Leu Cys His Pro Glu Glu Leu Val
             35                  40                  45

Leu Leu Gly His Ser Leu Gly Ile Pro Trp Ala Pro Leu Ser Ser Cys
 50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Cys Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 34
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is introduced
      between proline 101 and threonine 102.

<400> SEQUENCE: 34

Thr Pro Leu Gly Pro Ala Ser Ser Leu Pro Gln Ser Phe Leu Leu Lys
 1               5                  10                  15

Ser Leu Glu Gln Val Arg Lys Ile Gln Gly Asp Gly Ala Ala Leu Gln
             20                  25                  30

Glu Lys Leu Cys Ala Thr Tyr Lys Leu Cys His Pro Glu Glu Leu Val
             35                  40                  45

Leu Leu Gly His Ser Leu Gly Ile Pro Trp Ala Pro Leu Ser Ser Cys
 50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Cys Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

```
<210> SEQ ID NO 35
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is introduced
      between glutamic acid 122 and glutamic acid 123.

<400> SEQUENCE: 35

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Cys Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 36
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein  cysteine is introduced
      between leucine 124 and glycine 125.

<400> SEQUENCE: 36

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
```

```
            100                 105                 110
Phe Ala Thr Thr Ile Trp Gln Gln Met Glu Glu Leu Cys Gly Met Ala
        115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 37
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein  cysteine is introduced
      between methionine 126 and alanine 127.

<400> SEQUENCE: 37

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Cys Ala
        115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 38
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is introduced
      between glutamine 134 and glycine 135.

<400> SEQUENCE: 38

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
```

```
                  20                  25                  30
Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Cys Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 39
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is introduced
      between proline 138 and alanine 139.

<400> SEQUENCE: 39

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Cys Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 40
<211> LENGTH: 175
```

```
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is introduced
      between alanine 143 and phenylalanine 144.

<400> SEQUENCE: 40
```

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Cys
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

```
<210> SEQ ID NO 41
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein  cysteine is introduced
      between arginine 146 and arginine 147.

<400> SEQUENCE: 41
```

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

```
Phe Ala Thr Thr Ile Trp Gln Gln Met Glu Glu Leu Gly Met Ala Pro
                115                 120                 125

Ala Leu Gln Pro Thr Gly Ala Met Pro Ala Phe Ala Ser Ala Phe
        130                 135                 140

Gln Arg Cys Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 42
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is inserted between
      Arginine 169 and Histidine 170

<400> SEQUENCE: 42

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg Cys His Leu Ala Gln Pro
                165                 170                 175

<210> SEQ ID NO 43
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is inserted between
      histidine 170 and leucine 171

<400> SEQUENCE: 43

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
                20                  25                  30
```

```
Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
 50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
                100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Cys Leu Ala Gln Pro
                165                 170                 175
```

<210> SEQ ID NO 44
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is inserted between
      leucine 171 and alanine 172

<400> SEQUENCE: 44

```
Thr Pro Leu Gly Pro Ala Ser Ser Leu Pro Gln Ser Phe Leu Leu Lys
 1               5                  10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
 50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
                100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Cys Ala Gln Pro
                165                 170                 175
```

<210> SEQ ID NO 45
<211> LENGTH: 175
<212> TYPE: PRT
<213> ORGANISM: Homo sapiens

```
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is inserted between
      alanine 172 and glutamine 173

<400> SEQUENCE: 45

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Cys Gln Pro
                165                 170                 175

<210> SEQ ID NO 46
<211> LENGTH: 175
<212> TYPE: PRT
<213> ORGANISM: Homo sapiens
<220> FEATURE:
<221> NAME/KEY: VARIANT
<222> LOCATION: (1)..(175)
<223> OTHER INFORMATION: Sequence representing single cysteine insertion
      variant made on SEQ ID NO 3, wherein cysteine is inserted between
      glutamine 173 and proline 174

<400> SEQUENCE: 46

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125
```

```
Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Cys Pro
            165                 170                 175
```

<210> SEQ ID NO 47
<211> LENGTH: 176
<212> TYPE: PRT
<213> ORGANISM: Homo sapiens
<220> FEATURE:
<221> NAME/KEY: VARIANT
<222> LOCATION: (1)..(176)
<223> OTHER INFORMATION: Sequence representing wherein glycine, cysteine
      linker is added at C terminal of SEQ ID NO 3

<400> SEQUENCE: 47

```
Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro Gly Cys
                165                 170                 175
```

<210> SEQ ID NO 48
<211> LENGTH: 178
<212> TYPE: PRT
<213> ORGANISM: Homo sapiens
<220> FEATURE:
<221> NAME/KEY: VARIANT
<222> LOCATION: (1)..(178)
<223> OTHER INFORMATION: Sequence representing wherein glycine, glycine,
      serine, cysteine linker is added at C terminal of SEQ ID NO 3

<400> SEQUENCE: 48

```
Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
```

-continued

```
                 50                  55                  60
Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
                100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro Gly Gly
                165                 170                 175

Ser Cys

<210> SEQ ID NO 49
<211> LENGTH: 180
<212> TYPE: PRT
<213> ORGANISM: Homo sapiens
<220> FEATURE:
<221> NAME/KEY: VARIANT
<222> LOCATION: (1)..(180)
<223> OTHER INFORMATION: Sequence representing wherein glycine, glycine,
      glycine, serine, cysteine linker is added at C terminal
      of  SEQ ID NO 3

<400> SEQUENCE: 49

Thr Pro Leu Gly Pro Ala Ser Ser Leu Pro Gln Ser Phe Leu Leu Lys
 1               5                  10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
                100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro Gly Gly
                165                 170                 175

Gly Gly Ser Cys
            180

<210> SEQ ID NO 50
<211> LENGTH: 181
<212> TYPE: PRT
```

-continued

```
<213> ORGANISM: Homo sapiens
<220> FEATURE:
<221> NAME/KEY: VARIANT
<222> LOCATION: (1)..(181)
<223> OTHER INFORMATION: Sequence representing wherein serine, glycine,
      glycine, serine, glycine, glycine cysteine linker is added at C
      terminal of  SEQ ID NO 3

<400> SEQUENCE: 50

Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro Ser Gly
                165                 170                 175

Gly Ser Gly Gly Cys
            180

<210> SEQ ID NO 51
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: primer_bind
<222> LOCATION: (1)..(24)

<400> SEQUENCE: 51
ggatccatga cgccgctggg tccg                                              24

<210> SEQ ID NO 52
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: primer_bind
<222> LOCATION: (1)..(26)

<400> SEQUENCE: 52
aagcttttac ggctgtgcca ggtgac                                            26

<210> SEQ ID NO 53
<211> LENGTH: 21
```

```
<212> TYPE: DNA
<213> ORGANISM: Artificial Sequence
<220> FEATURE:
<223> OTHER INFORMATION: Synthetic
<220> FEATURE:
<221> NAME/KEY: primer_bind
<222> LOCATION: (1)..(21)

<400> SEQUENCE: 53
atgactccac tgggtccggc g                                            21

<210> SEQ ID NO 54
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: primer_bind
<222> LOCATION: (1)..(24)

<400> SEQUENCE: 54
atgactccat taggtccggc gagt                                         24

<210> SEQ ID NO 55
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: primer_bind
<222> LOCATION: (1)..(24)

<400> SEQUENCE: 55
atgactccat taggtccagc gagt                                         24

<210> SEQ ID NO 56
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: primer_bind
<222> LOCATION: (1)..(30)

<400> SEQUENCE: 56
atgactccat taggtccggc aagtagcctg                                   30

<210> SEQ ID NO 57
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: primer_bind
<222> LOCATION: (1)..(30)

<400> SEQUENCE: 57
atgactccat taggtccagc aagtagcctg                                   30

<210> SEQ ID NO 58
<211> LENGTH: 36
<212> TYPE: DNA
<213> ORGANISM: Artificial Sequence
<220> FEATURE:
<223> OTHER INFORMATION: Synthetic
```

```
<220> FEATURE:
<221> NAME/KEY: primer_bind
<222> LOCATION: (1)..(36)

<400> SEQUENCE: 58
atgactccat taggtccagc atctagcctg ccgcaa                              36

<210> SEQ ID NO 59
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: primer_bind
<222> LOCATION: (1)..(36)

<400> SEQUENCE: 59
atgactccgc tgggtccggc atctagcctg ccgcaa                              36

<210> SEQ ID NO 60
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: primer_bind
<222> LOCATION: (1)..(36)

<400> SEQUENCE: 60
atgactccgt taggtccggc atctagcctg ccgcaa                              36
```

POLYPEPTIDE EXHIBITING GRANULOCYTE-COLONY STIMULATING FACTOR ACTIVITY

INCORPORATION BY REFERENCE

The attached ASCII text file, identified as Sequence-listing-18-9-2020 ST25.txt, created Sep. 18, 2020 and 87.4 KB in size, is incorporated by reference herein.

FIELD OF THE INVENTION

The present invention generally relates to variants of Granulocyte-Colony Stimulating Factor ('G-CSF'), conjugates of the variants of G-CSF, methods for preparing such variants and conjugates and use of such variants or conjugates in therapy particularly neutropenia and leucopenia.

BACKGROUND OF THE INVENTION

Chemotherapy constitutes an indispensable component of the treatment of various forms of lymphomas and metastatic cancers. Chemotherapy is believed to suppress the hematopoietic system and thus weaken the host immune system. Neutropenia is the most critical haematological toxicity associated with the chemotherapy [Crawford, J. et al., Cancer, 2004. 100(2): p. 228-37]. Chemotherapy induced neutropenia is characterized by reduction in the number of neutrophils, which leads to predisposition of cancer patients to fatal infections and sepsis [Lyman, G. H., Clin Cornerstone, 2006. 8 Suppl 5: p. S12-8] Clinical management of neutropenia includes a lengthy hospital stay, along with administration of high-end antibiotics, which leads to tremendous escalation in cost of cancer treatment [Kuderer, N. M., et al., Cancer, 2006. 106(10): p. 2258-66]. The prophylactic and therapeutic administration of Colony-Stimulating Factors (CSFs) has proven to be extremely effective at significantly reducing the risk of neutropenia in patients receiving dose-intensive chemotherapy [Lyman, G. H. et al., Am J Med, 2002. 112(5): p. 406-11].

CSFs are cytokines that guide the hematopoietic system to generate specific types of white blood cells [Metcalf, D., Cancer, 1990. 65(10): p. 2185-95]. These factors were discovered in effort to grow the bone marrow cells in vitro [Bradley, T. R. et al. Nature, 1967. 213(5079): p. 926-7; Pluznik, D. H. et al. Experimental cell research, 1966. 43(3): p. 553-63 and Bradley, T. R. et al. The Australian journal of experimental biology and medical science, 1966. 44(3): p. 287-99]. Two types of CSFs are employed for prophylaxis of neutropenia namely—Granulocyte Macrophage-CSF (GM-CSF) and G-CSF. The most commonly used CSF is recombinant human G-CSF (rHuG-CSF). The administration of rHuG-CSF stimulates the production of mature functional neutrophils and thus reduces the risk of neutropenia [Welte, K., et al., Blood, 1996. 88(6): p. 1907-29]. Despite the discovery of the CSFs in 1960s, the human G-CSF was first purified and characterized by Moore and colleagues in 1985 from bladder carcinoma cell line 5637 [Welte, K., et al., Blood, 1996. 88(6): p. 1907-29]. This naturally produced G-CSF from the bladder carcinoma cell line 5637 is O-glycosylated and has molecular weight of 19.6 kDa that yield a product of 18.8 kDa upon treatment with O-glycanase [Souza, L. M., et al., Science, 1986. 232(4746): p. 61-5]. Nagata and co-workers utilized N-terminal amino acid sequencing to identify the cDNA sequence of G-CSF [Nagata, S., et al., Nature, 1986. 319(6052): p. 415-8]. Souza et al., further cloned, sequenced and expressed the identified sequence. The recombinant protein resulting from the expression of G-CSF cDNA in *Escherichia coli* was found to be capable of inducing proliferation and differentiation of human bone marrow cells [Souza, L. M., et al., Science, 1986. 232(4746): p. 61-5.]]. The administration of rHuG-CSF was approved by the United States Food and Drug Administration (the 'FDA') in 1991 and since then has been actively used for prevention of neutropenia, not only for patients receiving chemotherapy but also for patients suffering from leucopenia, AIDS, sepsis, and patients undergoing bone marrow transplantation [Keating, G. M., Drugs. 71(6): p. 679-707]. G-CSF binds to the extracellular immunoglobulin like domain and the cytokine receptor homologue domain on the Granulocyte-Colony Stimulating Factor Receptor (G-CSFR) This binding leads to homodimerization of G-CSFR and initiates the activation of JAK-STAT and mitogen-activated protein kinase pathways to execute the effects of G-CSF [Van de Geijn, G. J., et al., Rev Physiol Biochem Pharmacol, 2003. 149: p. 53-71]. The recombinant G-CSF is often produced in *E. coli* in the non-glycosylated form (e.g. Filgrastim) although a glycosylated protein (e.g. Lenograstim) produced in Chinese hamster ovary cells (CHO) is also in use [Fernandez-Varon, E. et al. Vet J, 2007. 174(1): p. 33-41]. Both non-glycosylated form and glycosylated forms have been reported to have equivalent activities and similar pharmacokinetics in cynomolgus monkeys[Tanaka, H., et al., Cytokine, 1997. 9(5): p. 360-9]. Filgrastim and the glycosylated Lenograstim, which is CHO derived G-CSF enhances the proliferation and differentiation of neutrophil precursors, migration of neutrophils in blood and tissues and increases the activity of mature neutrophils to prevent neutropenia. However, filgrastim has a half-life of 3-4 hr and needs to be administered daily [Kuwabara, T., et al. Drug metabolism reviews, 1996. 28(4): p. 625-58]

G-CSF is thought to be cleared using several different mechanisms, including receptor-mediated endocytosis [Kuwabara, T., et al., The American journal of physiology, 1995. 269(1 Pt 1): p. ET-9.], renal clearance [Kuwabara, T., et al., Pharmaceutical research, 1995. 12(10): p. 1466-9] and enzymatic degradation mechanism [El Ouriaghli, F., et al., Blood, 2003. 101(5): p. 1752-8.]. Several approaches have been employed to increase the serum half-life of rHuG-CSF. Various modifications such as conjugation with Polyethylene glycol ('PEG'), known as PEGylation [Molineux, G., Current pharmaceutical design, 2004. 10(11): p. 1235-44], conjugation with the sialic acid [Andersen, D. C. et al. Biotechnology and bioengineering, 1995. 47(1): p. 96-105], attachments with the human serum albumin [Halpern, W., et al., Pharmaceutical research, 2002. 19(11): p. 1720-9] etc. have been utilized. However, PEGylation has emerged as the method of choice for this purpose. PEGylation increases serum half-life of therapeutic proteins, including masking the protein's surface to shield it from proteases, antibodies and antigen processing cells and increasing the molecular size to reduce the renal ultrafiltration. Furthermore, PEG imparts favourable attributes on the polypeptides to improve the biological distribution and solubility [Harris, J. M. et al. Drug discovery, 2003. 2(3): p. 214-21]. In the year 2002, the FDA approved the use of PEGylated rHuG-CSF or Pegfilgrastim as a prophylactic drug in chemotherapy. PEGylated G-CSF has significantly improved serum half-life and thus is administered once per cycle of chemotherapy [Crawford, J., Drugs, 2002. 62 Suppl 1: p. 89-98] compared to daily dose of filgrastim.

The currently used PEGylated G-CSF conjugated with 20 kDa PEG molecule at the first amino acid on the N-terminal of the human G-CSF protein using reductive alkylation method [U.S. Pat. No. 5,824,784]. Although, this method results in efficient PEGylation of G-CSF, it is associated with heterogeneous PEGylation at the amino group of lysine residues present in protein in addition to PEGylation at the N-terminal amino group. G-CSF variants having multiple PEGylation have also been created for administration on the same-day treatment of chemotherapy-induced neutropenia [US 20090203601]. However, this method and other methods using conjugation of PEG molecule at the amino group of the N-terminal leads to a heterogeneous population of conjugated G-CSF due to variable levels of PEGylation. Such heterogeneous populations of drug molecules create difficulty in accurately predicting the biological activity. Recently, new methods of the site directed PEGylation had been described [Crawford, J., Drugs, 2002. 62 Suppl 1: p. 89-98, Goodson, R. J. and N. V. Katre, Bio/technology, 1990. 8(4): p. 343-6-30 and Xiong, C. Y., et al., Protein engineering, design & selection: PEDS, 2006. 19(8): p. 359-67] generating more homogenously PEGylated proteins.] One of the common methods of PEGylation uses cysteine of the protein or a suitably introduced cysteine residue for PEGylation [U.S. Pat. No. 5,766,897A].

G-CSF variants having multiple PEGylation have also been created for administration on the same-day treatment of chemotherapy-induced neutropenia [US 20090203601]. However, this method leads to a heterogeneous population of conjugated G-CSF due to variable levels of PEGylation. Such heterogeneous populations of drug molecules create difficulty in accurately predicting the biological activity.

Using this approach, cysteine 17 of the G-CSF was exploited for generating PEGylated version of G-CSF [Ishikawa, M., et al., Cell structure and function, 1992. 17(1): p. 61-5]. However, since the cysteine 17 is partially buried in a hydrophobic pocket, this method requires denaturation followed by PEGylation and the renaturation of the protein.

There is a need for new and improved polypeptides that exhibit G-CSF activity and conjugates thereof that can be used in therapy, for example in the treatment of neutropenia and leucopenia and at the same time do not suffer from the disadvantages of currently available polypeptides and their conjugates.

SUMMARY OF THE INVENTION

The present disclosure relates to a polypeptide exhibiting G-CSF activity. The polypeptide comprises at least one non-native cysteine residue at a site selected from the group consisting of $T_1CP_2$ (SEQ ID NO: 25), $P_2CL_3$ (SEQ ID NO: 26), $L_3CG_4$ (SEQ ID NO: 27), $G_4CP_5$ (SEQ ID NO: 28), $P_5CA_6$ (SEQ ID NO: 29), $A_6CS_7$ (SEQ ID NO: 30), $S_{96}CP_{97}$ (SEQ ID NO: 31), $P_{97}CE_{98}$ (SEQ ID NO: 32), $L_{99}CG_{100}$ (SEQ ID NO: 33), $P_{101}CT_{102}$ (SEQ ID NO: 34), $E_{122}CE_{123}$ (SEQ ID NO: 35), $L_{124}CG_{125}$ (SEQ ID NO: 36), $M_{126}CA_{127}$ (SEQ ID NO: 37), $P_{138}CA_{139}$ (SEQ ID NO: 39), $A_{143}CF_{144}$ (SEQ ID NO: 40), $R_{146}CR_{147}$ (SEQ ID NO: 41), $R_{169}CH_{170}$ (SEQ ID NO: 42), $H_{170}CL_{171}$ (SEQ ID NO: 43), $L_{171}CA_{172}$ (SEQ ID NO: 44), $A_{172}CQ_{173}$ (SEQ ID NO: 45), AND $Q_{173}CP_{174}$ (SEQ ID NO: 46) in an amino acid sequence having at least 90% identity to sequence set forth in SEQ ID NO: 2.

In an embodiment of the present disclosure, the polypeptide further comprises short linkers sequence at N- and/or C-terminal. Examples, of the short linked sequences include but are not limited to GC, GGSC, GGGGSC and SGGSGGC at C-terminal. Wherein the linker sequence consist from the group consist of (G)nC of nucleic acid sequence of SEQ ID NO: 47, (GGS)nC of nucleic acid sequence of SEQ ID NO: 48, (GGGGS)$_n$C of nucleic acid sequence of SEQ ID NO: 49 and (SGGSGG)nC of nucleic acid sequence of SEQ ID NO: 50 at N- and/or C-terminal in an amino acid sequence having at least 90% identity to sequence set forth in SEQ ID NO: 3.

The present disclosure also relates to a nucleic acid construct encoding a polypeptide exhibiting granulocyte-colony stimulating factor activity and having sequence set forth in SEQ ID NO. 1.

The present disclosure also relates to polypeptide conjugates comprises the said polypeptide covalently attached to at least one molecule of polyethylene glycol ('PEG').

The present disclosure further relates to an expression vector comprising the said nucleic acid construct.

The present disclosure also relates to a host cell comprising the said expression vector.

The present disclosure also relates to a method of treating a patient suffering from neutropenia. The method comprises administering to the patient a therapeutic amount of the said polypeptide or the said conjugate.

The present disclosure also relates to use of the said polypeptide or the said conjugate for the preparation of a pharmaceutical composition for treating neutropenia.

The present disclosure also relates to a pharmaceutical composition comprising the said polypeptide or conjugate and at least one pharmaceutically acceptable carrier or excipient.

BRIEF DESCRIPTION OF DRAWINGS

FIG. 5. Depicts preferred position for cysteine substitution for site specific PEGylation of G-CSF.

FIG. 6. Depicts preferred position for cysteine insertion for site specific PEGylation of G-CSF.

FIG. 7. Depicts N- & C- terminal cysteine insertion and substitution sites for PEGylation.

FIG. 8. Depicts a sequence list of variants of G-CSF for cysteine substitution and insertion.

DETAILED DESCRIPTION

Figure 1:
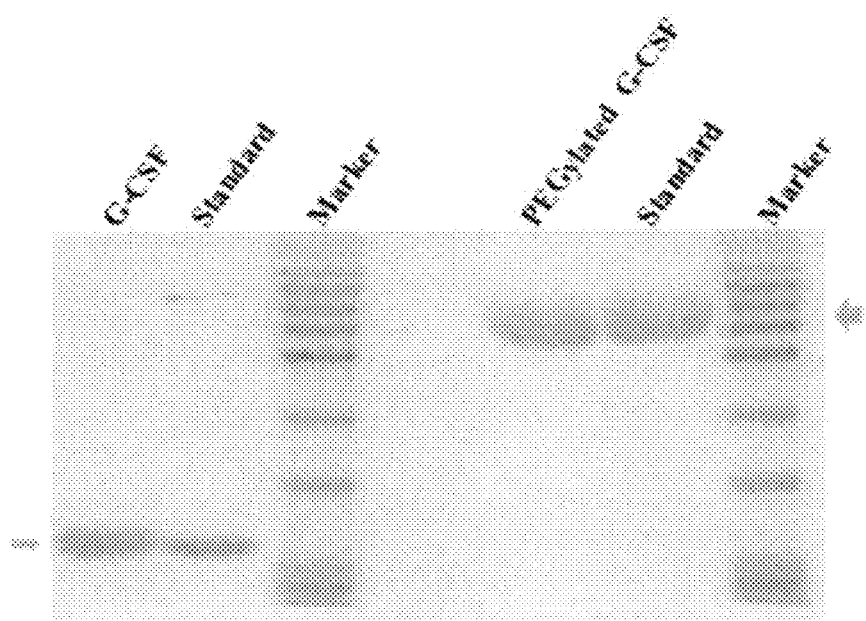
FIG. 1. Depicts the purified rHuG-CSF and PEGylated rHuG-CSF. The engineered human G-CSF construct was overexpressed in *E. coli* cells. The purified rHuG-CSF protein was conjugated with the 20 kDa PEG-aldehyde derivative. The conjugated product was then purified using cation exchange chromatography followed by hydrophobic interaction chromatography (HIC) or Size-exclusion chromatography. The purified rHuG-CSF (indicated by thin arrow) and PEG-conjugated rHuG-CSF (indicated by thick arrow) were analysed on non-denaturing PAGE and stained with Coomassie brilliant blue. The purified G-CSF and N-terminal 20 kDa PEGylated rHuG-CSF are found to be more than 95% pure, when analysed by SDS-PAGE.

The present disclosure relates to polypeptides exhibiting G-CSF activity, conjugates of the said polypeptides and nucleic acid sequences encoding the said polypeptides. The present disclosure further relates to pharmaceutical compositions comprising said polypeptides and conjugates, methods of treatment using the said polypeptides, conjugates and compositions and use of said polypeptides in manufacture of preparation of a pharmaceutical composition for treating neutropenia.

In the present disclosure, amino acid names are used as defined by the Protein Data Bank (PDB) (www.pdb.org), which is based on the IUPAC nomenclature (IUPAC Nomenclature and Symbolism for Amino Acids and Peptides (residue names, atom names etc.), Eur. J. Biochem., 138, 9-37 (1984) together with their corrections in Eur. J. Biochem., 152, 1 (1985).

Thus, the following symbols have been used for the amino acids.

| Amino Acid | Symbol |
|---|---|
| Alanine | Ala or A |
| Cysteine | Cys or C |
| Aspartic acid | Asp or D |
| Glutamic acid | Glu or E |
| Phenylalanine | Phe or F |
| Glycine | Gly or G |
| Histidine | His or H |
| Isoleucine | Ile or I |
| Lysine | Lys or K |
| Leucine | Leu or L |
| Methionine | Met or M |
| Asparagine | Asn or N |
| Proline | Pro or P |
| Glutamine | Gln or Q |
| Arginine | Arg or R |
| Serine | Ser or S |
| Threonine | Thr or T |

-continued

| Amino Acid | Symbol |
|---|---|
| Valine | Val or V |
| Tryptophan | Trp or W |
| Tyrosine | Tyr or Y |

The terminology used for identifying amino acid positions/substitutions is illustrated as follows P5 indicates that position number 5 on the amino acid sequence of the disclosed polypeptide is occupied by proline.

$P_5CA_6$ indicates that a non-native cysteine residue is inserted between proline at position number 5 and alanine at position number 6 of the amino acid sequence with SEQ IN NO: 3.

The term cysteine derivative, cysteine variant and or G-CSF variant is used for the polypeptide with cysteine 17 replaced with serine or alanine and consist of cysteine substitution and or addition at selected site/s.

The term "exhibiting G-CSF activity" is intended to indicate that the polypeptide or conjugate has one or more of the functions of native G-CSF, in particular rHuG-CSF with the amino acid sequence shown in SEQ ID NO: 2 including the capability to bind to a G-CSF receptor (Fukunaga et al., J. Bio. Chem., 265:14008, 1990).

The present disclosure relates to a polypeptide exhibiting G-CSF activity. The polypeptide comprises at least one non-native cysteine residue at a site selected from the group consisting of $T_1CP_2$ (SEQ ID NO: 25), $P_2CL_3$ (SEQ ID NO: 26), $L_3CG_4$ (SEQ ID NO: 27), $G_4CP_5$ (SEQ ID NO: 28), $P_5CA_6$ (SEQ ID NO: 29), $A_6CS_7$ (SEQ ID NO: 30), $S_{96}CP_{97}$ (SEQ ID NO: 31), $P_{97}CE_{98}$ (SEQ ID NO: 32), $L_{99}CG_{100}$ (SEQ ID NO: 33), $P_{101}CT_{102}$ (SEQ ID NO: 34), $E_{122}CE_{123}$ (SEQ ID NO: 35), $L_{124}CG_{125}$ (SEQ ID NO: 36), $M_{126}CA_{127}$ (SEQ ID NO: 37), $P_{138}CA_{139}$ (SEQ ID NO: 39), $A_{143}CF_{144}$ (SEQ ID NO: 40), $R_{146}CR_{147}$ (SEQ ID NO: 41), $R_{169}CH_{170}$ (SEQ ID NO: 42), $H_{170}CL_{171}$ (SEQ ID NO: 43), $L_{171}CA_{172}$ (SEQ ID NO: 44), $A_{172}CQ_{173}$ (SEQ ID NO: 45), and $Q_{173}CP_{174}$ (SEQ ID NO: 46) in an amino acid sequence having at least 90% identity to sequence set forth in SEQ ID NO: 3.

In an embodiment of the present disclosure, more than one non-native cysteine residue is inserted at two or more aforementioned sites. The particular number of cysteine residues to be inserted depends upon the desired nature and degree of conjugation.

In an embodiment, the amino acid sequence comprises substitution of cysteine at C17 with serine residue.

In another embodiment, the polypeptide further comprises short linkers sequence at N- and/or C-terminal. Examples, of the short linker sequences include but are not limited to GC, GGSC, GGGGSC and SGGSGGC. The significance of these linker sequence is covered in subsequent example.

The present disclosure also relates to a polypeptide conjugate. The polypeptide conjugate comprises the said polypeptide covalently attached to at least one molecule of PEG.

The insertion of cysteine residue in the amino acid sequence makes the latter more susceptible to conjugation. Also, it allows optimization of the conjugation pattern. In an embodiment the at least one molecule of PEG is a methoxy PEG maleimide derivative. The size of the PEG molecule is in the range of 5,000 to 40,000 daltons. In accordance with specific embodiments the size is selected from 20,000, 30,000 and 40,000 daltons.

The present disclosure also relates to a nucleic acid sequence encoding the disclosed peptide. The nucleic acid construct comprises a sequence set forth in sequence with SEQ ID NO: 1

The present disclosure also relates to an expression vector comprising the nucleic acid construct. The expression vector comprises other elements necessary for the expression of the nucleic acid in a host cell for example having strong promoter such as T7 RNA polymerase.

The present disclosure also relates to a host cell expressing the disclosed polypeptide. The host cell is obtained by transforming a suitable cell with the disclosed expression vector. Any suitable method of transformation of host cell may be used. Examples, of suitable host cells include prokaryotic host cells such as *E. coli* but are not limited to it.

In other aspect, the present disclosure relates to a pharmaceutical composition comprising the polypeptide or the polypeptide conjugate and at least one pharmaceutically acceptable carrier or excipient. The pharmaceutical composition may be formulated in a variety of forms. Examples of such forms include a liquid or gel, or lyophilized, or any other suitable form. The polypeptide or the polypeptide conjugate can be formulated into pharmaceutical compositions in a manner known per se in the art to result in a polypeptide pharmaceutical that is sufficiently storage-stable and is suitable for administration to humans or animals.

In yet another aspect, the present disclosure relates to method for treating various forms of leucopenia or neutropenia using the disclosed polypeptide, conjugate or composition. In particular, the disclosed polypeptide, conjugate or composition may be used to prevent infection in cancer patients undergoing certain types of radiation therapy, chemotherapy bone marrow transplantations and in liver regeneration.

In another aspect, the present disclosure relates to use of the disclosed polypeptide, conjugate or the polypeptide for the preparation of a pharmaceutical composition for treating various forms of neutropenia or leucopenia.

The invention is further described in the non-limiting examples below.

EXAMPLES

Example 1. The Nucleic Acid Construct Synthesis, Cloning and Expression

The cDNA sequence of human G-CSF was codon optimized for expression in *E. coli* (Genescript). This sequence was cloned into the BamHI and HindIII sites of the expression vector pET23a (Novagen) using forward primer IMT1: 5' GGATCCATGACGCCGCTGGGTCCG 3' with SEQ ID NO: 51 and reverse primer IMT2: 5' AAGCTTTTACGGCTGTGCCAGGTGAC 3' with SEQ ID NO: 52. This construct was used to transform BL21 (DE3) *E. coli* strain from Novagen. In order to increase the yield of the codon optimized rHuG-CSF sequence, in silico analysis of DNA and RNA sequence of codon-optimized construct was performed. This analysis suggested formation of hairpins and highly stable secondary structure at 5' prime end of the mRNA transcript, raising possibility that the mRNA transcripts might be hindering the translation. Translationally silent mutagenesis of the gene at 5' prime end was performed to disrupt and/or reduce the mRNA secondary structures by replacement of GC rich codons (that are more likely to promote secondary structure in the mRNA transcript) with AT rich codons at suitable positions. Through a series of translationally silent mutagenesis, several sequences were created and analysed for increase in the protein yield compared to that of the native sequence.

```
IMT3:
                                          (SEQ ID NO: 53)
5' ATG ACT CCA CTG GGT CCG GCG 3'

IMT4:
                                          (SEQ ID NO: 54)
5' ATG ACT CCA TTA GGT CCG GCG AGT 3'

IMT5:
                                          (SEQ ID NO: 55)
5' ATG ACT CCA TTA GGT CCA GCG AGT 3'

IMT6:
                                          (SEQ ID NO: 56)
5' ATG ACT CCA TTA GGT CCG GCA AGT AGC CTG 3'

IMT7:
                                          (SEQ ID NO: 57)
5' ATG ACT CCA TTA GGT CCA GCA AGT AGC CTG 3'

IMT8:
                                          (SEQ ID NO: 58)
5' ATG ACT CCA TTA GGT CCA GCA TCT AGC CTG CCG
CAA 3'

IMT9:
                                          (SEQ ID NO: 59)
5' ATG ACT CCG CTG GGT CCG GCA TCT AGC CTG CCG
CAA 3'

IMT10:
                                          (SEQ ID NO: 60)
5' ATG ACT CCG TTA GGT CCG GCA TCT AGC CTG CCG
CAA 3'
```

IMT8 (with SEQ ID NO: 58) resulted in maximal destabilisation of the secondary structure in the mRNA and resulted in significantly higher protein expression. This sequence was cloned into the NdeI and HindIII sites of the expression vector pET23a and pET9b (Novagen). This engineered construct has resulted in 2.5 fold increase in rHuG-CSF protein yield.

```
Human sequence
5' ATG ACC CCC CTG GGC CCT GCC AGC TCC CTG

E. Coli Codon optimized
5' ATG ACG CCG CTG GGT CCG GCG AGT AGC CTG
(GC Content-74%)

Silent mutations (IMT8) of nucleic acid
sequence of SEQ ID NO: 58:
5' ATG ACT CCA TTA GGT CCA GCA TCT AGC CTG
(GC Content-48%)

Amino acids
 M   T   P   L   G   P   A   S   S   L
```

Example 2. Over-Expression and Purification of G-CSF and its Variants

The codon optimized cDNA sequence of human G-CSF with incorporated IMT8 sequence of nucleic acid sequence of SEQ ID NO: 58 at the 5' prime end was cloned into the NdeI and HindIII sites of the expression vector pET23a & pET9b. This engineered construct (SEQ ID NO: 1) was then used to transform BL21 (DE3) strain of *E. coli*.

This construct was utilized in subsequent G-CSF variants engineering. G-CSF variants were created by using standard protocols of site directed mutagenesis or by PCR using primers with desired changes for introduction or substitution of cysteine at a particular position in the coding sequence.

Figure 2:
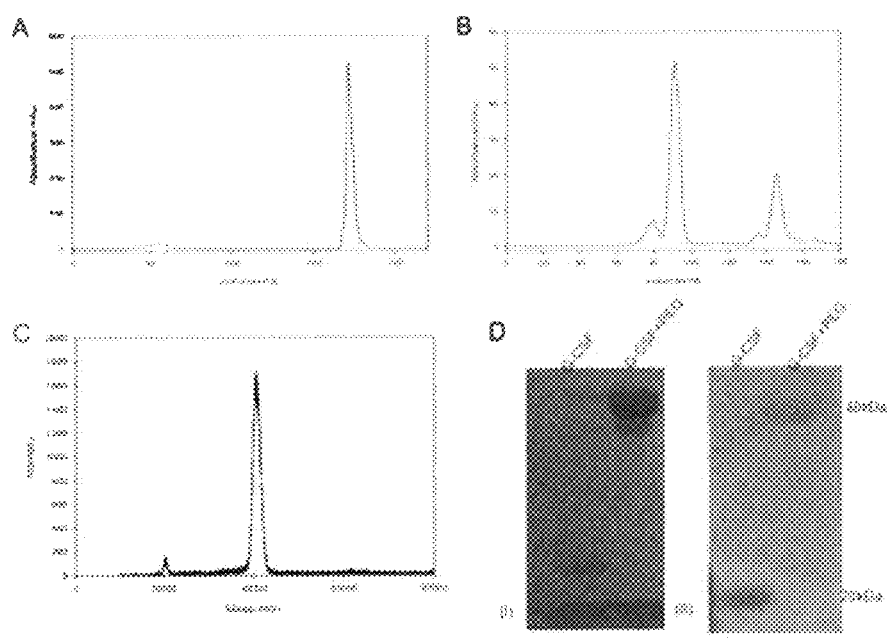
FIG. 2. Depicts the representative profile of PEGylation of G-CSF variants. The rHuG-CSF variant was overexpressed in *E. coli* cells and purified using methods described earlier. The purified protein was conjugated with the 20 kDa PEG using PEG-maleimide derivative. The conjugated product was then purified using cation exchange chromatography (a) followed by HIC or size-exclusion chromatography (b). The PEG-conjugated G-CSF was then analysed using MALDI-TOF mass spectrometry (c). It was observed that the majority of G-CSF was conjugated to the 20 kDa PEG and had molecular weight of approximately 40 kDa. (d) The purified G-CSF PEGylated with 20 kDa was then analysed on non-denaturing PAGE and stained with barium iodide that specifically stains PEG (panel I). Native G-CSF without PEG conjugation was not detected while the PEG conjugated protein was clearly visible. The samples were also analysed with Coomassie brilliant blue staining (panel II). Native G-CSF was only detected in Coomassie staining. An increase in the molecular weight was clearly visible upon conjugation with 20 kDa PEG. It was observed that the purified G-CSF conjugated with the 20 kDa run at the expected size of 40 kDa.

The purified rHuG-CSF expressed in *E. coli* was analysed using the reducing and non-reducing PAGE. This analysis revealed that the purified G-CSF exhibits a single protein band at the right size, and is comparable to the commercial product (FIG. 1). Broadly, the rHuG-CSF protein isolation and purification involved following steps.

i. Overnight cell culture was used to inoculate 1 litre media and once the $OD_{600}$ reached ~0.4-0.6, the cell culture was induced with 0.5 mM Isopropyl β-D-1-thiogalactopyranoside (IPTG).

ii. After 4 hrs, the cells were harvested by centrifugation. The cells were lysed using sonication and the inclusion bodies were isolated.

iii. The inclusion bodies from step ii were washed thrice using following buffer components (50 mM Tris-Cl, pH 8.0, 1 mM EDTA buffer with 2% Triton X-100, 1% Na-deoxycholate or 1 M NaCl).

iv. Washed inclusion bodies from step iii were solubilised using urea, wherein the preferred concentration is in the range of about 2 M to about 4 M urea.

v. The isolated G-CSF was subjected to two-step refolding process.

vi. The refolded G-CSF was purified using cation exchange chromatography.

vii. The cation exchange purified sample was subjected to hydrophobic interaction chromatography (HIC) and/or size exclusion chromatography (SEC). The resins and columns were purchased from GE Healthcare Life Sciences.

viii. In case of cysteine variants of G-CSF, the purified G-CSF variant from step vi was used to conjugate PEG of varying size.

ix. The 5 fold molar excess of thiol specific PEG was used to conjugate rHuG-CSF variant in sodium phosphate or Tris buffer, preferred pH range of the buffer was about 6.5 to about 7.5.

x. The N-terminal amino acid specific PEG was conjugated to rHuG-CSF in sodium phosphate, sodium acetate or sodium citrate buffer wherein the preferred buffer concentration was in the range of 25 mM to about 100 mM. The reaction is performed in the presence of reducing agent, sodium cyanoborohydrate (wherein the preferred concentration range is about 15 mM to about 25 mM). The preferred pH for the reaction was in the range of 4.0-5.5. The PEG's for both the chemistry were from JenKem Technology, USA.

xi. The PEGylated species were purified by cation exchange chromatography using SP Sepharose or more preferably MacroCap SP resins (from GE Healthcare Life Sciences), followed by HIC and/or SEC.

xii. The samples were run on SDS PAGE and stained with barium iodide for visualizing the PEGylated G-CSF (FIG. 2).

Example 2. Selection of G-CSF Protein Regions for Generating Cysteine Variants

G-CSF is the primary growth factor involved in the proliferation, maturation, and differentiation of the neutrophilic-precursor cells to effector neutrophils. Extensive structural and functional studies over the years have gathered vast information about the regions of G-CSF, that play a critical role in its binding with the G-CSF receptor (G-CSFR) to initiate the signal transduction cascade that play an important role in the neutrophil proliferation. The structure of G-CSF complexed with the ligand-binding region of the G-CSF receptor in a 2:2 conformation has been solved [Aritomi, M., et al., Nature, 1999. 401(6754): p. 713-7 and Tamada, T., et al., Proceedings of the National Academy of Sciences of the United States of America, 2006. 103(9): p. 3135-40]

The solution structure of the G-CSF has also been solved using NMR spectroscopy [Zink, T., et al., Biochemistry, 1994. 33(28): p. 8453-63]. The G-CSF possesses four alpha-helical bundle structure, and these helices are labelled as A, B, C & D starting from N-terminal. There are three primary sites on the G-CSF that interact with G-CSFR protein. Another important feature of the G-CSF is the presence of five cysteine residues; four of those are involved in disulphide bonds. G-CSF has one free cysteine at position 17 and has intramolecular disulphide bonds at position 36-42 and 64-74. These disulphide bonds are necessary for biological activity of G-CSF. Whereas, the substitution of cysteine at position 17 with serine yield a mutant G-CSF protein that is fully functional [U.S. Pat. No. 4,810,643]. In the current invention, all the cysteine substitution variants have been derived from the G-CSF variant in which cysteine 17 has been changed to serine or alanine. The recombinant human G-CSF protein sequence has been assigned SEQ ID NO: 2. The cysteine 17 replaced to serine 17 variant protein sequence is assigned SEQ ID NO: 3. For all subsequent cysteine variant generation, G-CSF template with SEQ ID NO: 3 was used.

Cysteine mutations are utilized for PEGylation to increase the in vivo half-life of the therapeutic proteins [28]. Currently used PEGylated-G-CSF is conjugated to a 20 kDa PEG molecule at the N-terminal using reductive alkylation. However, covalent PEG modification can also be performed at the rationally selected residues of the G-CSF to further improve the half-life of G-CSF. To select the specific residues in G-CSF, or the functionally irrelevant regions of G-CSF for cysteine substitution, computational biology approach was utilized for detecting the surface accessible amino acids. The existing structural information from G-CSF structural studies was also employed to locate the regions suitable for cysteine substitution. The preferred sites for PEGylation in region proximal to Helix A are—T1, P2, L3, G4, P5, A6, S7 and S8; in Helix A are R22, E33, K34; in AB loop K40, L61; in Helix B Q90; in BC loop P97, E98, L99; in Helix C P101, Q119, E122 and E123; CD loop, P128 and P138; in Helix D R146, R147, R169, H170, L171 and A172; and in region distal to Helix D Q173 and P174. These preferred sites for cysteine substitution of native amino acid are given in FIG. 5.

This example provide most preferred sites for cysteine substitution—T1C (SEQ ID NO: 4), L3C (SEQ ID NO: 5), G4C (SEQ ID NO: 6), P5C (SEQ ID NO: 7), Q90C (SEQ ID NO: 8), P97C (SEQ ID NO: 9), E98C (SEQ ID NO: 10), P101C (SEQ ID NO: 11), Q119C (SEQ ID NO: 12), E122C (SEQ ID NO: 13), E123C (SEQ ID NO: 14), P128C (SEQ ID NO: 15), P138C (SEQ ID NO: 16), R146C (SEQ ID NO: 17), R147C (SEQ ID NO: 18), R169C (SEQ ID NO: 19), H170C (SEQ ID NO: 20), L171C (SEQ ID NO: 21), A172C (SEQ ID NO: 22) Q173C (SEQ ID NO: 23), P141C (SEQ ID NO: 24).

In one aspect, provided is a method to further confirm the solvent accessibility of the G-CSF in solution, wherein, protease degradation mapping was performed. Herein, G-CSF was subjected to protease digestion with several proteases such as trypsin, chymotrypsin and elastase using both in silico and in vitro analyses. The N- or C-terminal of the digested fragments were sequenced to identify the most prominent site/s of protease digestion. The protein degradation revealed the surface exposed regions which could be more accessible for PEGylation. Several residues in these region were utilized in this example, wherein cysteine substitution and addition was selected for generation of G-CSF variants for improved PEGylation efficiency. The structural integrity of G-CSF variants where analysed by computational biology approach. The secondary structure of the G-CSF variants was analysed using Circular Dichroism (CD) spectroscopy. The variants having similar structures to the wild type G-CSF protein and wherein their structural integrity is maintained could be used for PEG conjugation. The cysteine substitution and insertion variants in close proximity or at the potential protease sites used for site specific PEGylation could impart protease resistance and prolong the in vivo circulation half-life.

In another aspect of this invention, provided is a method wherein instead of cysteine substitution, cysteine addition was preferred. Most preferably in unstructured loop regions which is not involved in G-CSF receptor binding and thus will not impede the biological activity. The predictions made using computational biology was combined with the structural data of G-CSF and residues for cysteine insertion mutagenesis were selected. Values of absolute surface accessibility were considered for selecting the specific residues for cysteine substitution and as well as addition. FIG. 6, provides the details of the most preferable positions for cysteine additions to create G-CSF variant are listed. This was ensured that the structural integrity of G-CSF is not compromised due to substitution or addition of cysteine. The solvent accessibility would increase the efficiency of the PEG conjugation of G-CSF, besides shielding the protein from the protease to increase the in vivo half-life. The most preferable sites for cysteine addition are—$T_1CP_2$ (SEQ ID NO: 25), $P_2CL_3$ (SEQ ID NO: 26), $L_3CG_4$ (SEQ ID NO: 27), $G_4CP_5$ (SEQ ID NO: 28), $P_5CA_6$ (SEQ ID NO: 29), $A_6CS_7$ (SEQ ID NO: 30), $S_{96}CP_{97}$ (SEQ ID NO: 31), $P_{97}CE_{98}$ (SEQ ID NO: 32), $L_{99}CG_{100}$ (SEQ ID NO: 33), $P_{101}CT_{102}$ (SEQ ID NO: 34), $E122CE_{123}$ (SEQ ID NO: 35), $L_{124}CG_{125}$ (SEQ ID NO: 36), $M_{126}CA_{127}$ (SEQ ID NO: 37), $P_{138}CA_{139}$ (SEQ ID NO: 39), $A_{143}CF_{144}$ (SEQ ID NO: 40), $R_{146}CR_{147}$ (SEQ ID NO: 41), $R_{169}CH_{170}$ (SEQ ID NO: 42), $H_{170}CL_{171}$ (SEQ ID NO: 43), $L_{171}CA_{172}$(SEQ ID NO: 44), $A_{172}CQ_{173}$ (SEQ ID NO: 45), and $Q_{173}CP_{174}$(SEQ ID NO: 46).

Example 3. Modification of N- and/or C-Terminal of G-CSF to Create Variants for Efficient Pegylation G-CSF has four helix connected with loops and also N- and C-terminal regions have unstructured regions. Importantly, computational analysis has suggested that these N- and C-terminal of G-CSF are solvent accessible. Addition of flexible amino acid linker sequence at the C terminal of the protein could also increase the flexibility and solubility of the region. The flexible linkers are generally rich in small or polar amino acids such as glycine and serine but can also consists of amino acids such as threonine, alanine, lysine and glutamic acid.

Using this information, in this example, short flexible linker sequences containing cysteine was added at N- and/or C-terminal of the G-CSF to further increase the flexibility and solvent accessibility of cysteine added for PEG conjugation. These cysteine variants were further modified by conjugating cysteine reactive methoxy PEG maleimide. The addition of linker sequences containing cysteine would not alter the overall conformation of molecule and thus would not reduce the activity of the therapeutic protein. However, due to better solvent accessibility, these variants could possess higher PEG conjugation efficiency. Furthermore, in silico analysis also indicated that the cysteine with smaller amino acids such as glycine or a serine linker could enhance the solvent accessibility. The most preferred cysteine containing linker sequences are—(G)nC (SEQ ID NO: 47), (GGS)nC (SEQ ID NO: 48), $(GGGGS)_n$ C (SEQ ID NO: 49) and (SGGSGG)nC (SEQ ID NO: 50) (as given in FIG. 7). In these sequences linker length is n=1 to 4. These variants will impart improved solvent accessibility of cysteine for PEGylation. The cysteine variants generated have been assigned unique SEQ IDs. FIG. 7, provides the details of the most preferable positions for N and C terminal cysteine additions to create G-CSF variant.

Moreover, the solved structure of the G-CSF suggests that the N- and C-terminal unstructured loops are in close proximity. Two cysteine residues at both the two terminals could result in formation of disulphide bond under appropriate conditions. Such a disulphide bond formation will result in a circularized variants of the G-CSF. Earlier published literature suggests that circularization of protein enhances the thermal stability, protease resistance and in vivo half-life.

Example 4. Conjugation of PEG to rHuG-CSF to Increase Half-Life

PEGylation is one of the important methods used to create modified variants of the therapeutic proteins for improving their overall half-life in vivo. Currently used PEGylated G-CSF is conjugated to a 20 kDa PEG molecule at the N-terminal using reductive alkylation. Cysteine mutations have been demonstrated to facilitate PEGylation of the therapeutic proteins. In this invention several cysteine variants of G-CSF were provided to facilitate site specific PEGylation (FIG. 8). These G-CSF variants are expected to have comparable biological activity to the commercially available G-CSF since the core of the protein involved in interaction with the G-CSF receptor has not been changed. However, due to their design and PEGylation, they would possess the advantage of improved bioavailability due to slow degradation. Such PEGylated variants of G-CSF are expected to possess longer serum half-life.

Figure 3:
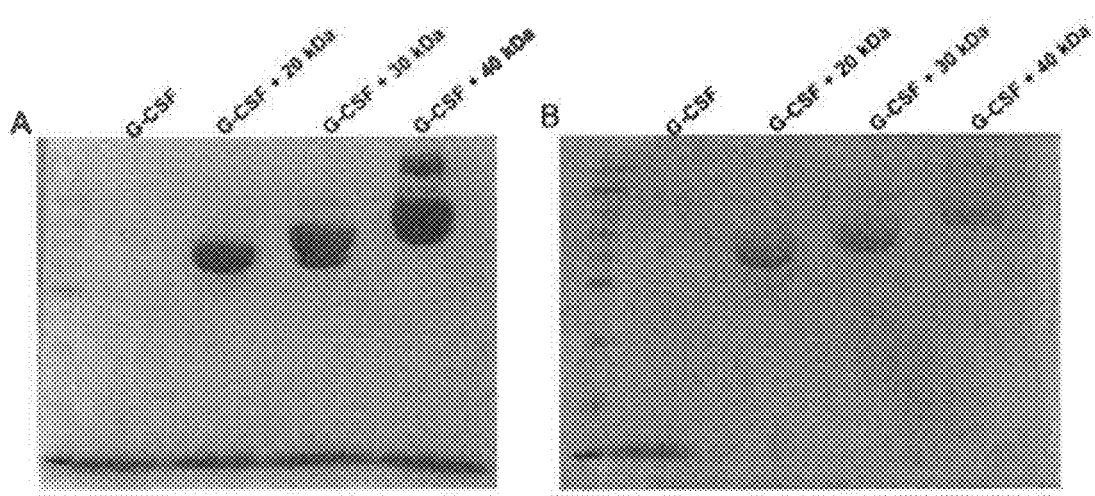
FIG. 3. Depicts representative profile of conjugation of G-CSF variant with 20 kDa, 30 kDa and 40 kDa PEG. As described above, the novel G-CSF variant was conjugated with 20 kDa, 30 kDa and 40 kDa PEG using PEG-maleimide derivatives. The PEG conjugated variants were purified using the cation exchange chromatography followed by HIC or size-exclusion chromatography purification steps. The purified conjugated products along with unmodified control were then run on 12% non-reducing PAGE and stained with barium iodide staining for visualizing PEG (a) or with Coomassie brilliant blue staining for protein (b). Corresponding increase in the molecular weight was observed upon conjugation with 20 kDa, 30 kDa and 40 kDa PEG and non-PEGylated control was detected only in Coomassie stained gel.

Furthermore, different sizes of PEG ranging from 5000 daltons-40,000 daltons could be conjugated to these variants to increase their half-life and bioavailability. To confirm efficient PEGylation of newly designed variants MALDI-TOF analysis could be performed. FIGS. 2 and 3 show the purification strategy evolved for PEGylated G-CSF variant, as is seen by the resolution of purified PEGylated product in SDS-PAGE stained with Coomassie brilliant blue for visualization of proteins and barium iodide for visualization of the PEGylated variants. The higher molecular weight of the PEGylated variant was also confirmed with Matrix-assisted laser desorption/ionization time of flight (MALDI-TOF) Mass Spectrometry. To access the secondary structure of the variants, CD spectroscopy was performed.

Example 5. Analysis of Bioactivity of G-CSF and PEGylated Variants by Cell-Based Assay To analyse the biological activity of rHuG-CSF and its variants, cell proliferation assays were performed. The biological activity of rHuG-CSF was determined by its ability to proliferate murine myeloblastic NFS-60 cells. In these assays the metabolic activity of proliferating cells is measured through reduction of tetrazolium reagent such as XTT. The cells were treated with various concentrations of standard, rHuG-CSF and its PEGylated variants for 48 hr and their metabolic activity was then assessed using the XTT reagent. The biological activity of commercially available filgrastim and the lab produced rHuG-CSF and its variant/s was found to be comparable. The result from this could demonstrate that the mutations in the G-CSF has not resulted in the compromise of the biological activity.

Figure 4:
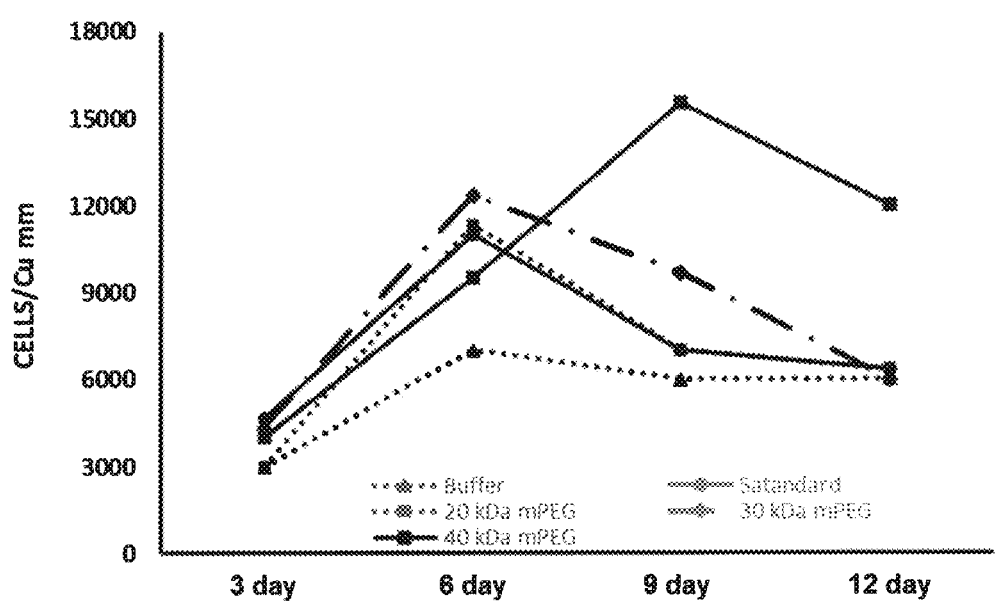
FIG. 4. Depicts comparison between in vivo activity of standard and G-CSF variant conjugated with 20 kDa, 30 kDa and 40 kDa methoxy PEG maleimide.

Example 6. In Vivo Biological Activity and Half-Life of the Novel G-CSF Variants Male BALB/c mice, 12-14 weeks old, were used in the current study for analysing the biological activity and in vivo half-life of the novel G-CSF variants engineered in this study. Towards this, mice were acclimatized for a week, and neutropenia was induced in mice using intra-peritoneal injection of cyclophosphamide (200 mg/kg) as per standard procedures. To confirm induction of neutropenia, blood was withdrawn and total leucocytes counts (TLC) were measured. One-day, post induction of neutropenia, "Sham" or Mock (having buffer only), therapeutically active G-CSF (commercially available), and the engineered variants were independently administered as the single subcutaneous dose (up to 1 mg/Kg) or multiple dosages of 125 µg/Kg for the span of 4-7 days. After G-CSF treatment, the blood samples were withdrawn, and TLC counts are determined for following 5-10 days. The lab-made native-like, and commercial filgrastim exhibited comparable specific activity. Interestingly, we observed that the treatment of neutropenia with the PEGylated G-CSF variants (i.e. newly constructed PEGylated cysteine variants) resulted in accelerated recovery from neutropenia. Similarly, for estimating the in vivo half-life, independent groups of mice were injected with either the Sham sample, commercially available G-CSF and novel G-CSF variants. Blood samples were withdrawn, and the presence of G-CSF in serum was estimated using the commercially available G-CSF Elisa kit. These data clearly showed that the variant possess higher biological activity and longer in vivo half-lives compared to original unmodified G-CSF (FIG. 4).

Advantages of the Invention

The disclosed polypeptides are more susceptible to conjugation. Also, the disclosed polypeptides allow optimization of the conjugation pattern. The disclosed conjugates exhibit significantly longer serum half-life, a therapeutically advantageous property. The disclosed conjugates, therefore, can be used on the same day of administration of chemotherapy. Site specific PEGylation overcomes the problem of product heterogeneity and loss of biological activity that arises due to the conventionally used amine-PEGylation.

Site specific PEGylation allows the protein to be selectively conjugated with PEG at a unique single, double or more, predetermined, site(s). Such sites make the characterization of the polypeptide more robust and the biological activity can be relatively accurately predicted and made commensurate with different regimens of treatments. Further, the site of PEGylation is at residues that are solvent accessible making PEGylation highly efficient and the product more homogenous.

The present invention provides cysteine variants of G-CSF and their application to generate PEG conjugated variants, with potential for significantly longer serum half-life, a therapeutically advantageous property, and thus could be used on the same day of administration of chemotherapy.

REFERENCES

1. Crawford, J., D. C. Dale, and G. H. Lyman, *Chemotherapy-induced neutropenia: risks, consequences, and new directions for its management.* Cancer, 2004. 100(2): p. 228-37.
2. Lyman, G. H., *Risks and consequences of chemotherapy-induced neutropenia.* Clin Cornerstone, 2006. 8 Suppl 5: p. S12-8.
3. Kuderer, N. M., et al., *Mortality, morbidity, and cost associated with febrile neutropenia in adult cancer patients.* Cancer, 2006. 106(10): p. 2258-66.
4. Lyman, G. H., N. M. Kuderer, and B. Djulbegovic, *Prophylactic granulocyte colony-stimulating factor inpatients receiving dose-intensive cancer chemotherapy: a meta-analysis.* Am J Med, 2002. 112(5): p. 406-11.
5. Metcalf, D., The colony stimulating factors. *Discovery, development, and clinical applications.* Cancer, 1990. 65(10): p. 2185-95.
6. Bradley, T. R., D. Metcalf, and W. Robinson, *Stimulation by leukaemic sera of colony formation in solid agar cultures by proliferation of mouse bone marrow cells.* Nature, 1967. 213(5079): p. 926-7.
7. Pluznik, D. H. and L. Sachs, *The induction of clones of normal mast cells by a substance from conditioned medium.* Experimental cell research, 1966. 43(3): p. 553-63.
8. Bradley, T. R. and D. Metcalf, *The growth of mouse bone marrow cells in vitro.* The Australian journal of experimental biology and medical science, 1966. 44(3): p. 287-99.
9. Welte, K., et al., *Filgrastim (r-metHuG-CSF): the first 10 years.* Blood, 1996. 88(6): p. 1907-29.
10. Welte, K., et al., *Purification and biochemical characterization of human pluripotent hematopoietic colony-stimulating factor.* Proceedings of the National Academy of Sciences of the United States of America, 1985. 82(5): p. 1526-30.
11. Souza, L. M., et al., *Recombinant human granulocyte colony-stimulating factor: effects on normal and leukemic myeloid cells.* Science, 1986. 232(4746): p. 61-5.
12. Nagata, S., et al., *Molecular cloning and expression of cDNA for human granulocyte colony-stimulating factor.* Nature, 1986. 319(6052): p. 415-8.
13. Keating, G. M., *Lenograstim: a review of its use in chemotherapy-induced neutropenia, for acceleration of neutrophil recovery following haematopoietic stem cell transplantation and in peripheral blood stem cell mobilization.* Drugs. 71(6): p. 679-707.
14. van de Geijn, G. J., et al., *Granulocyte colony-stimulating factor and its receptor in normal hematopoietic cell development and myeloid disease.* Rev Physiol Biochem Pharmacol, 2003. 149: p. 53-71.
15. Fernandez-Varon, E. and L. Villamayor, *Granulocyte and granulocyte macrophage colony-stimulating factors as therapy in human and veterinary medicine.* Vet J, 2007. 174(1): p. 33-41.
16. Tanaka, H., et al., *Three types of recombinant human granulocyte colony-stimulating factor have equivalent biological activities in monkeys.* Cytokine, 1997. 9(5): p. 360-9.
17. Kuwabara, T., S. Kobayashi, and Y. Sugiyama, *Pharmacokinetics and pharmacodynamics of a recombinant* human granulocyte colony-stimulating factor. Drug metabolism reviews, 1996. 28(4): p. 625-58.
18. Kuwabara, T., et al., *Receptor-mediated clearance of G-CSF derivative nartograstim in bone marrow of rats.* The American journal of physiology, 1995. 269(1 Pt 1): p. E1-9.
19. Kuwabara, T., et al., *Renal clearance of a recombinant granulocyte colony-stimulating factor, nartograstim, in rats.* Pharmaceutical research, 1995. 12(10): p. 1466-9.
20. El Ouriaghli, F., et al., Neutrophil elastase enzymatically antagonizes the in vitro action of G-CSF: implications for the regulation of granulopoiesis. Blood, 2003. 101(5): p. 1752-8.
21. Molineux, G., *The design and development of pegfilgrastim (PEG-rmetHuG-CSF, Neulasta).* Current pharmaceutical design, 2004. 10(11): p. 1235-44.
22. Andersen, D. C. and C. F. Goochee, *The effect of ammonia on the O-linked glycosylation of granulocyte colony-stimulating factor produced by chinese hamster ovary cells.* Biotechnology and bioengineering, 1995. 47(1): p. 96-105.
23. Halpern, W., et al., *Albugranin, a recombinant human granulocyte colony stimulating factor (G-CSF) genetically fused to recombinant human albumin induces prolonged myelopoietic effects in mice and monkeys.* Pharmaceutical research, 2002. 19(11): p. 1720-9.
24. Harris, J. M. and R. B. Chess, *Effect of pegylation on pharmaceuticals.* Nature reviews. Drug discovery, 2003. 2(3): p. 214-21.
25. Crawford, J., *Pegfilgrastim administered once per cycle reduces incidence of chemotherapy-induced neutropenia.* Drugs, 2002. 62 Suppl 1: p. 89-98.
26. Kinstler, O. B., et al., *N-terminally chemically modified protein compositions and methods,* 1998, Google Patents.
27. Soni, B., et al., *Method for the treatment of neutropenia by administration of a multi-pegylated granulocyte colony stimulating factor (G-CSF) variant,* 2008, Google Patents.
28. Braxton, S. M., *Cysteine-pegylated proteins,* 1998, Google Patents.
29. Goodson, R. J. and N. V. Katre, *Site-directed pegylation of recombinant interleukin-2 at its glycosylation site.* Bio/technology, 1990. 8(4): p. 343-6.
30. Xiong, C. Y., et al., *Development of tumor targeting anti-MUC-1 multimer: effects of di-scFv unpaired cysteine location on PEGylation and tumor binding.* Protein engineering, design & selection: PEDS, 2006. 19(8): p. 359-67.
31. Ishikawa, M., et al., *The substitution of cysteine 17 of recombinant human G-CSF with alanine greatly enhanced its stability.* Cell structure and function, 1992. 17(1): p. 61-5.
32. Kozlowski, A. and J. M. Harris, *Improvements in protein PEGylation: pegylated interferons for treatment of hepatitis C.* Journal of controlled release: official journal of the Controlled Release Society, 2001. 72(1-3): p. 217-24.
33. Zhai, Y., et al., *Enhanced circulation half-life of site-specific PEGylated rhG-CSF: optimization of PEG molecular weight.* Journal of biotechnology, 2009. 142(3-4): p. 259-66.
34. Aritomi, M., et al., *Atomic structure of the GCSF-receptor complex showing a new cytokine-receptor recognition scheme.* Nature, 1999. 401(6754): p. 713-7.
35. Tamada, T., et al., *Homodimeric cross-over structure of the human granulocyte colony-stimulating factor (GCSF) receptor signaling complex.* Proceedings of the National Academy of Sciences of the United States of America, 2006. 103(9): p. 3135-40.
36. Zink, T., et al., *Structure and dynamics of the human granulocyte colony-stimulating factor determined by NMR spectroscopy. Loop mobility in a four-helix-bundle protein.* Biochemistry, 1994. 33(28): p. 8453-63.
37. Berna, M. and F. M. Veronese, *G-CSF conjugates with peg,* 2005, Google Patents.

PATENT REFERENCES

| | | | |
|---|---|---|---|
| U.S. Pat. No. 6,608,183 | 8/2003 | Cox, III; George N | 530/399 |
| U.S. Pat. No. 7,309,781 | 12/2007 | Cox, III; George N | 530/399 |
| U.S. Pat. No. 7,253,267 | 8/2007 | Cox, III; George N | 530/399 |
| U.S. Pat. No. 7,214,779 | 5/2007 | Cox, III; George N | 530/399 |
| U.S. Pat. No. 7,232,885 | 6/2007 | Cox, III; George N | 530/351 |
| U.S. Pat. No. 7,345,149 | 3/2008 | Cox, III; George N | 530/351 |
| U.S. Pat. No. 7,314,921 | 1/2008 | Cox, III; George N | 530/399 |
| U.S. Pat. No. 7,629,314 | 12/2008 | Cox, III; George N | 514/1.1 |
| U.S. Pat. No. 7,795,396 | 9/2010 | Cox, III; George N | 530/351 |
| U.S. Pat. No. 7,732,572 | 6/2010 | Cox, III; George N | 530/351 |
| U.S. Pat. No. 7,964,184 | 6/2011 | Cox, III; George N | 424/85.5 |
| U.S. Pat. No. 8,133,480 | 3/2012 | Cox, III; George N | 424/85.2 |
| U.S. Pat. No. 7,153,943 | 12/2012 | Cox, III, et al. | 530/399 |
| U.S. Pat. No. 7,824,669 | 11/2010 | Cox, III, et al. | 424/85.1 |
| U.S. Pat. No. 8,148,500 | 4/2012 | Cox, III, et al. | 530/399 |
| U.S. Pat. No. 7,947,655 | 5/2011 | Cox, III, et al. | 541/21.2 |
| U.S. Pat. No. 7,560,101 | 7/2009 | Cox, III, et al. | 424/85.1 |
| U.S. Pat. No. 8,455,434 | 6/2013 | Cox; George N. | 514/7.6 |
| U.S. Pat. No. 8,841,426 | 9/2014 | Kang, et al. | 530/399 |
| U.S. Pat. No. 5,824,784 | 10/1998 | Kinstler, et al. | 530/399 |
| U.S. Pat. No. 8,093,032 | 1/2012 | Kumar, et al. | 435/216 |
| US 20090203601 | 8/2009 | Soni, et al. | 514/1.1 |
| US 20130165637 | 6/2013 | Xiaoqiang, et al. | 530/362 |
| US6831158 | 12/2004 | Nissen, et al. | 530/397 |
| US7994124B2 | 8/2011 | Cox, et al. | 514/7.6 |
| EP0668354A1 | 4/1989 | Shaw et al. | C12N 15/27 |

We claim:

1. A polypeptide exhibiting granulocyte-colony stimulating factor activity, the polypeptide comprising an amino acid sequence selected from the group consisting of SEQ ID NO: 25-37 and 39-46.

2. The polypeptide as claimed in claim 1, wherein the polypeptide further comprises a short linker sequence selected from the group consisting of residues 175 to 176 of SEQ ID NO: 47, residues 175-178 of SEQ ID NO: 48, residues 175-180 of SEQ ID NO:49 and residues 175-181 of SEQ ID NO: 50 at an C-terminus.

3. The polypeptide as claimed in claim 1, wherein the polypeptide is conjugated to at least one molecule of polyethylene glycol.

4. The polypeptide as claimed in claim 3, wherein the polyethylene glycol is a methoxy PEG maleimide derivative.

5. The polypeptide as claimed in claim 3, wherein the size of the polyethylene molecule ranges from 5,000 to 40,000 daltons.

6. A codon-optimized nucleic acid construct encoding a polypeptide exhibiting granulocyte colony stimulating factor activity as claimed in claim 1, wherein cDNA sequence of the polypeptide is incorporated with an oligodeoxynucleotide sequence selected from the group consisting of SEQ ID NO: 58(IMT8), SEQ ID NO: 59(IMT9), and SEQ ID NO: 60(IMT10), at the 5' end.

7. An expression vector comprising the nucleic acid construct as claimed in claim 6.

8. A host cell comprising the expression vector as claimed in claim 7.

9. A method of treating a patient suffering from neutropenia, the method comprising administering to the patient a therapeutic amount of the polypeptide as claimed in claim 1.

10. A pharmaceutical composition comprising the polypeptide as claimed in claim 1 and at least one pharmaceutically acceptable carrier or excipient.

* * * * *